United States Patent [19]
Slater et al.

[11] Patent Number: 5,986,756
[45] Date of Patent: Nov. 16, 1999

[54] SPECTROSCOPIC PROBE WITH LEAK DETECTION

[75] Inventors: Joseph B. Slater, Dexter; Michael J. Pelletier, Saline, both of Mich.

[73] Assignee: Kaiser Optical Systems, Ann Arbor, Mich.

[21] Appl. No.: 09/032,078

[22] Filed: Feb. 27, 1998

[51] Int. Cl.$^6$ ............................ G01N 21/64; G01N 21/65
[52] U.S. Cl. .................. 356/301; 356/318; 250/458.1
[58] Field of Search .................. 356/301, 317, 356/318; 250/458.1, 461.1

[56] References Cited

U.S. PATENT DOCUMENTS

| | | | |
|---|---|---|---|
| 4,283,937 | 8/1981 | Aoki et al. | 73/49.3 |
| 5,074,663 | 12/1991 | Wintertone et al. | 356/244 |
| 5,120,129 | 6/1992 | Farquharson et al. | 356/246 |
| 5,185,521 | 2/1993 | Kvasnik et al. | 356/301 |
| 5,341,206 | 8/1994 | Pittaro et al. | 356/301 |
| 5,452,082 | 9/1995 | Sanger et al. | 356/246 |
| 5,452,084 | 9/1995 | Mitchell et al. | 356/301 |
| 5,476,004 | 12/1995 | Kingsford | 73/40 |

*Primary Examiner*—F. L. Evans
*Attorney, Agent, or Firm*—Gifford, Krass, Groh, Sprinkle, Anderson & Citkowski, PC

[57] ABSTRACT

An optical probe assembly, which may be used with or without optical fibers for remote operation, incorporates a leak-detecting capability. A source such as a laser is used for optically exciting at least a portion of a sample substance, causing wavelengths characteristic of the sample to be emitted along a collection path for reception by spectral analysis means. The same laser or a different source is employed for optically exciting a point within a test region, causing wavelengths characteristic of any substances contained or entering into the test region to merge with those of the sample within the collection path.

16 Claims, 3 Drawing Sheets

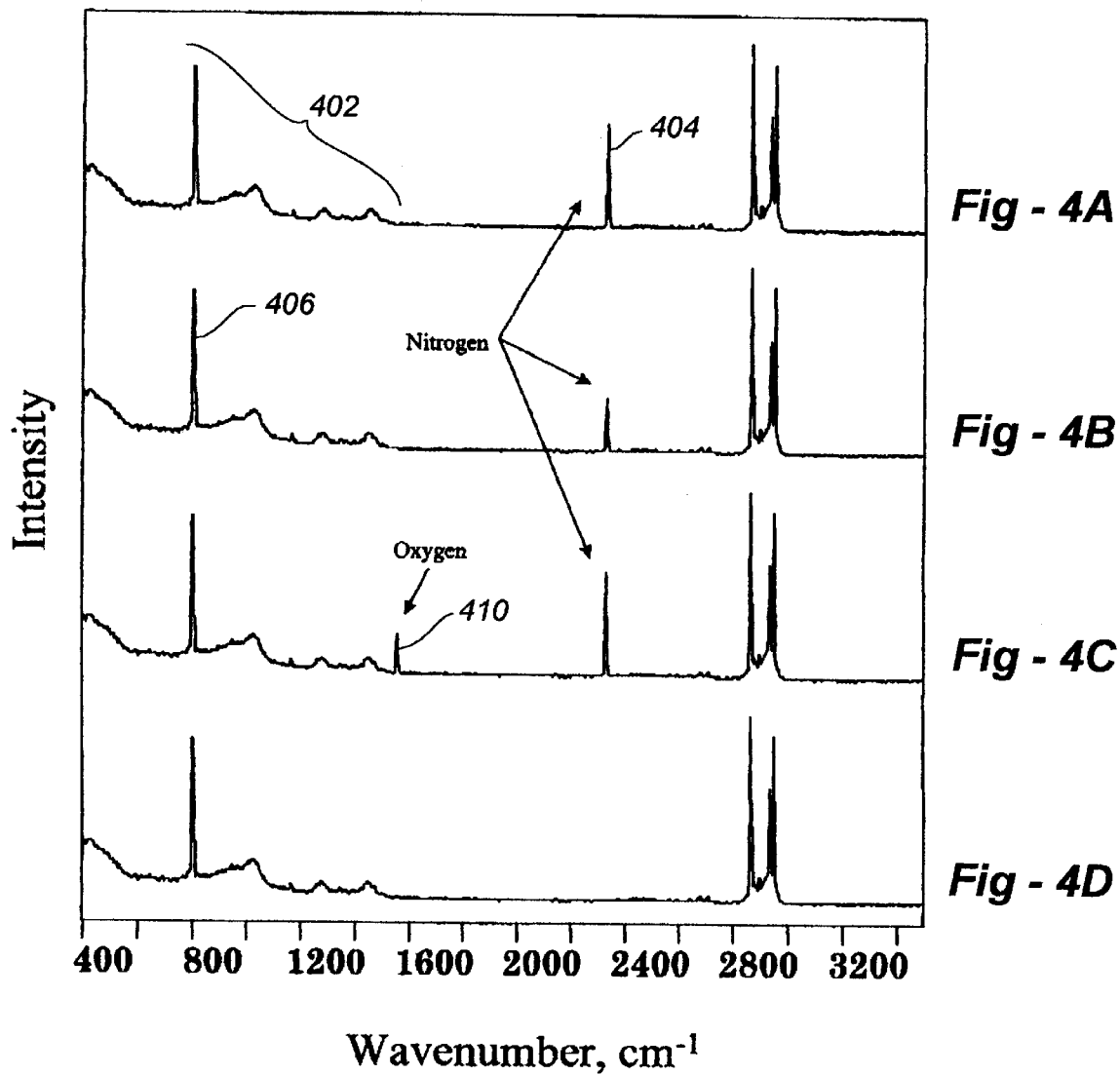

SPECTROSCOPIC PROBE WITH LEAK DETECTION

FIELD OF THE INVENTION

This invention relates generally to spectral analysis such as Raman and fluorescence detection and, in particular, to a probe incorporating a leak-detection capability.

BACKGROUND OF THE INVENTION

Induced radiative effects such as Raman scattering and fluorescence have become extremely valuable tools associated with the non-destructive determination of molecular constituents. To characterize a composition in a remote or hostile environment, optical fibers may advantageously be used to deliver excitation energy to a sample under investigation and to carry scattered radiation back to means for spectral analysis. An excitation source path may take the form of a laser providing a stimulus at an appropriate wavelength coupled to an input fiber, and a collection path may comprise one or more additional fibers carrying return radiative information to a spectral analysis tool such as a spectrograph.

Fiber-optic probes make it possible to collect optical information such as Raman spectra without having to place the material being characterized inside a spectrometer housing. Such probes therefore simplify the interfacing of spectroscopic systems to chemical processes, and allow analytical instruments to be located remotely from hostile environments in need of spectroscopic monitoring.

The first remote fiber optic probes for Raman spectroscopy, reported by the McCreery group in the early 1980's, used a single optical fiber to deliver laser light to the sample and a single optical fiber to collect light scattered by the sample. This dual-fiber approach offered important benefits. For one, the probe could be made less than one millimeter in diameter, making Raman measurements possible for samples with limited accessibility. In addition, the probe could be placed directly into a hostile sample, since only silica and the encapsulation material were exposed.

More modern imaging probes, however, utilize multiple optical components at or near the distal ends of the excitation and collection fibers. As described in commonly assigned U.S. Pat. No. 5,377,004, entitled REMOTE OPTICAL MEASUREMENT PROBE, merging of the excitation radiation into a combined excitation/collection path preferably takes place proximate to the remote end of the fibers, requiring a beam combiner to be located near the sample. In addition, to prevent laser wavelengths from entering into the collection fiber(s), one or more rejection filters are preferably situated in the probehead as well.

Increasingly, imaging probes of the type just described are being utilized to monitor processes involving hazardous chemicals. Because of the hazardous nature of the materials, it is necessary to ensure that insertion of the probes into pipes or vessels will not leak into the surrounding environment. However, due to the need for additional components in the optical paths from the sample to the tips of the excitation and collection fibers in an imaging probe, leak paths may be created along the various optical paths unless sufficient safeguards are provided.

SUMMARY OF THE INVENTION

This invention resides in an optical probe assembly including a leak-detecting capability. According to one aspect, the invention recognizes that a sample may physically leak along the path used for optical measurement, and takes advantage of this potentiality by placing one or more excitation/collection points along the path itself. The spectra emitted at each point, if any, combines with the spectra emitted by the sample, enabling common instrumentation to monitor containment integrity in addition to sample composition. Although the apparatus is preferably used in conjunction with a remote probehead coupled to analytical instrumentation through one or more optical fibers, The approach is equally applicable to any optical path monitoring situation.

A leak-detecting optical probe assembly according to the invention includes means for optically exciting a sample substance, causing wavelengths characteristic of the sample to be emitted along a collection path, and means for optically exciting a test region such that emission spectra associated with the test region, if any, enter into the collection path. The test region may be empty, evacuated, or contain a known substance, preferably in liquid or gaseous form.

The assembly may use a single source of radiation for optically exciting the sample and the test region. For example, the excitation may be delivered along a path which is counter-propagating with respect to the collection path. As an alternative, the sample and test region may be excited separately, including the use of different excitation sources. The collection path carrying spectra characteristic of the sample and the test region may be delivered to the same analytical instrumentation, which may be used to monitor the absolute or relative composition of the test region for leak-detection purposes.

BRIEF DESCRIPTION OF THE DRAWING

FIG. 4A is a wavelength/intensity diagram showing spectra of interest relative to a peak associated with a known substance according to the invention;

FIG. 4B illustrates how, with some of the sample leaking into the volume containing the known substance, the peak of the known substance may diminish, thereby providing information indicative of a leak;

FIG. 4C illustrates how, if air leaks into the volume containing the known substance, an oxygen peak might appear for use in leak detection; and FIG. 4D illustrates a serious breach of the known-substance containment volume, resulting in the absence of a signature for the known substance.

DETAILED DESCRIPTION OF THE INVENTION

Figure 1A:
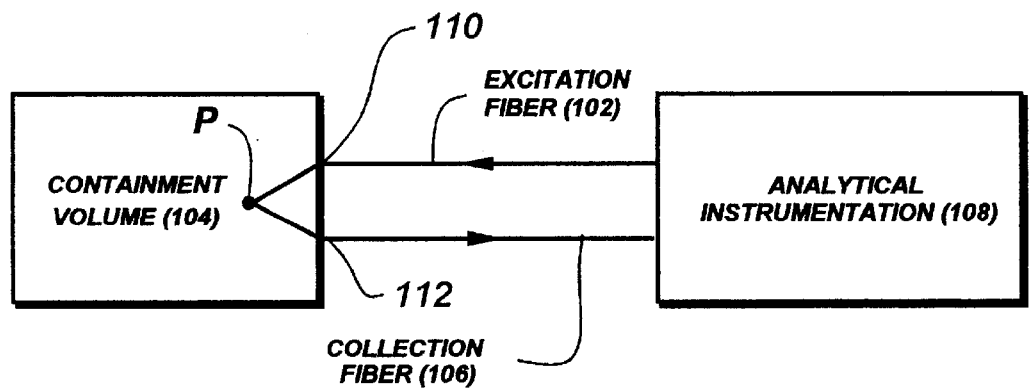
FIG. 1A is a schematic drawing which shows leak paths associated with a prior-art non-imaging style probe.
Figure 1B:
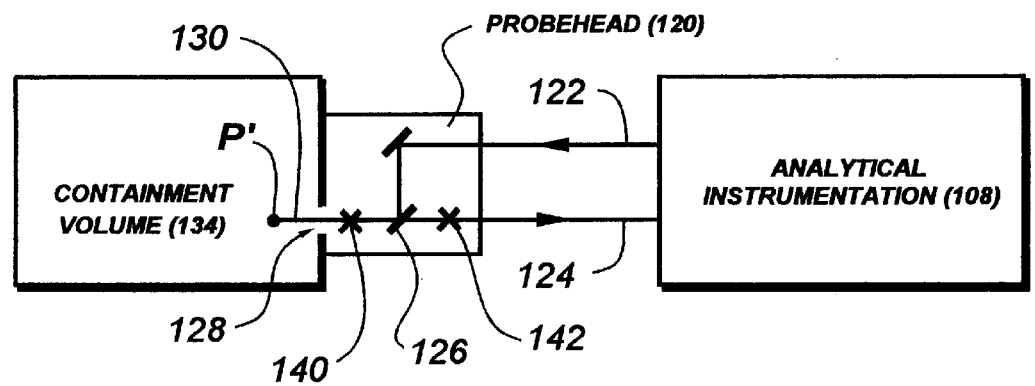
FIG. 1B is a schematic drawing which illustrates an existing remote optical measurement probe of the type to which the invention is applicable.

FIGS. 1A and 1B help to illustrate basic principles underlying this invention. FIG. 1A illustrates a non-imaging type of fiber-optic probe wherein an excitation fiber 102 carries excitation energy to a point P of a sample within a containment volume 104, and a collection fiber 106 is used to carry an emission spectrum representative of the sample back to analytical instrumentation 108. Although leaking of the sample from the volume 104 presents a problem, the leak rate may be maintained at a relatively low value due to the reduced physical size of the points of entry 110 and 112 of the excitation and collection fibers, respectively.

FIG. 1B illustrates a different configuration to which the present invention is applicable, wherein an imaging probehead 120 containing various optical components is used to couple an excitation fiber 122 and a collection fiber 124 to the sample point P' within a sample containment volume 134. The various optical components typically include a beam combiner 126 used to create a combined excitation/collection path 130 which is focused onto the point P'. The use of this combined excitation/collection path may be result in a larger entry 128 into the containment vessel 134 thereby creating additional challenges to leak prevention. Thus adding a leak detection capability to the probe will provide immediate indication that a leak has occurred.

According to this invention, the emission spectra of points along the collection path are detected in addition to the spectrum representative of the sample, thereby affording means whereby a chemical composition within the probehead 120 itself may be monitored. In one embodiment, the combined excitation/collection path 130 may be focused to a point 140 within the probehead 120, which may be used to determine if any outside substances have leaked into the probehead 120, including the sample material contained within volume 134. As an alternative, points along the collection path such as point 142 may be separately excited if it is desired to monitor other points within the probehead 120. The invention therefore affords an early advance warning should there be a compromise in the integrity.

Figure 2:
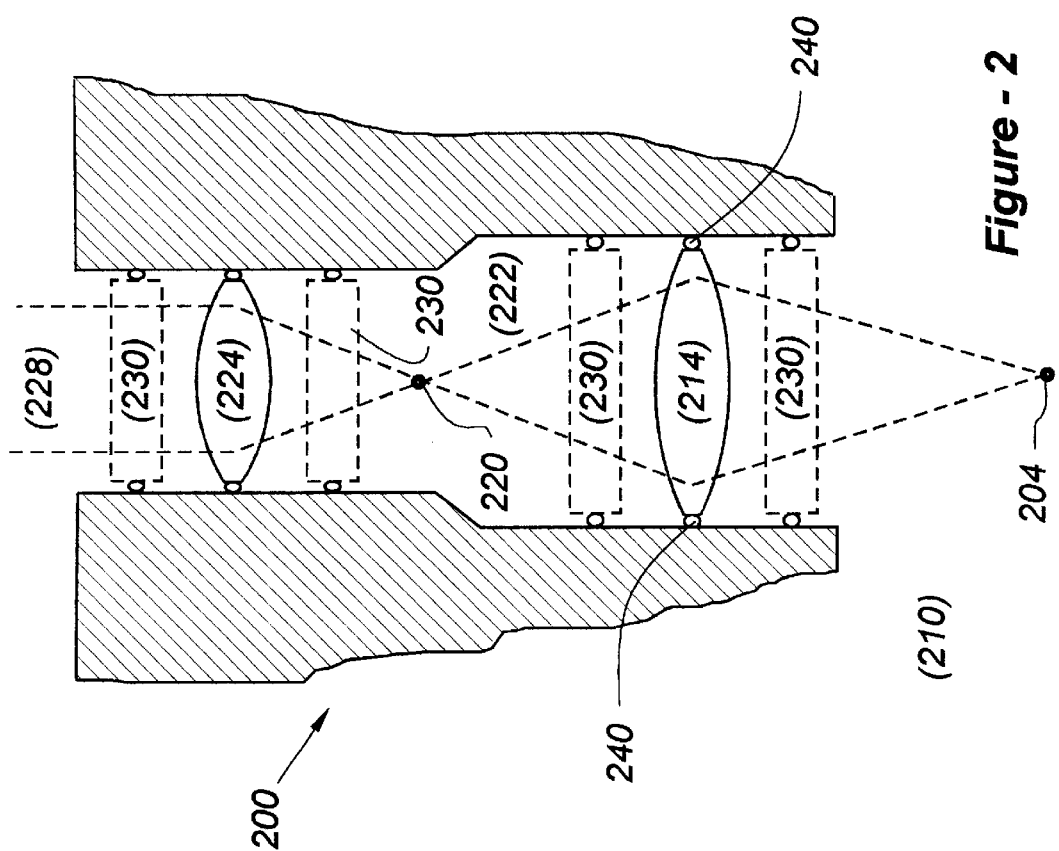
FIG. 2 illustrates, in partial cross-section, a spectroscopic probe according to the invention.

FIG. 2 is a drawing, in partial cross-section, of a preferred embodiment of the invention. This drawing represents a close-up view of the area 128 of FIG. 1B, wherein, in this case, optical path 228 includes both excitation and collection wavelengths in counter-propagating directions. By virtue of optical element 214, a point 204 will be established within sample volume 210, which corresponds to P' within volume 134 of FIG. 1B.

In addition, a second point 220 will be established within a test region 222. Assuming that test region 222 includes a known substance, the path 228 will now carry the spectral signatures of both the sample and the known substance, with excitation occurring primarily at points 204 and 220, respectively.

Optical windows 230 may be placed at any of the locations depicted in broken-line form, for example, to protect the elements 214 and 224. Such windows may be tilted, wedged or include anti-reflective coatings to enhance transmission. The windows 230 are optional, however, since, in the most basic configuration, only two elements are required to form the chamber 222, and the optical elements 214 and 224 may be used for this purpose by themselves, assuming appropriate seals such as 240 are used peripherally therearound.

The test region 222 may be empty, evacuated, or filled with any substance having a known or recognizable spectral signature, including mixtures of materials, whether in gaseous, liquid or solid form (i.e., as an amorphous solid or crystal). If empty or evacuated, entry of any substance from outside the probehead, including the sample, whether known or unknown, will be excited at point 220, causing an emission characteristic of the material to enter into the combined path 228. As further alternatives, the side walls of the test region 222 may be coated with a powder that goes into solution in the event that a liquid leaks into the region 222, and such powder may cause a dramatic change in the signal level received. For example, the powder may fluoresce, resulting in highly conspicuous peaks, or the powder may cause the encroaching liquid to become at least semi-opaque thereby dramatically reducing signal levels. As a further option, one or more of the windows may be tilted with respect to the optical path, with the geometry being arranged so that one set of signals are received in that the region 222 is gas-filled, with the optics changing due to the alteration of refraction index in the event that the region 222 fills with a liquid.

In the preferred embodiment, test region 222 is filled with nitrogen by purging and backfilling. Nitrogen is advantageous, since its Raman signature is often very different from sample spectra of interest, and therefore typically located in an isolated wavelength region.

Figure 3:
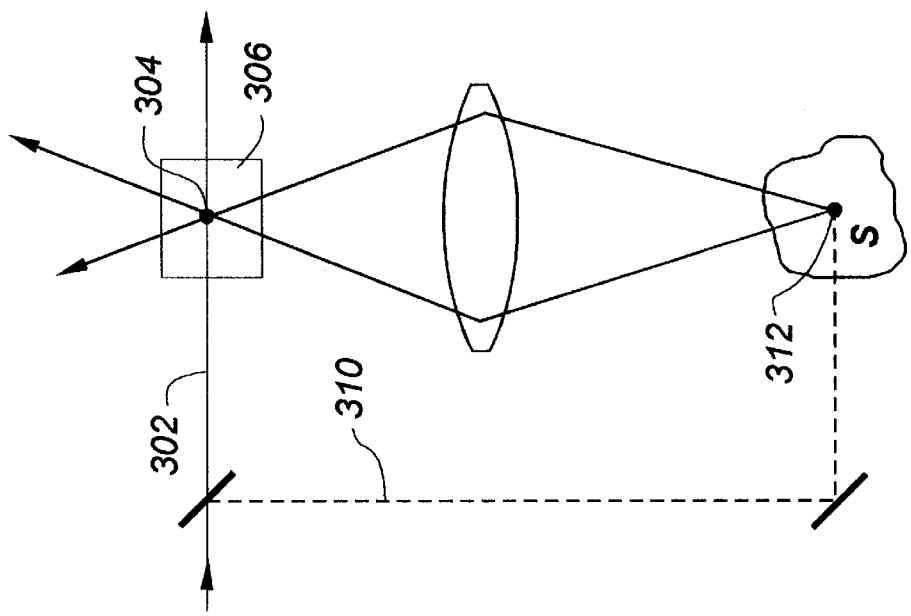
FIG. 3 illustrates an embodiment of the invention wherein a sample and a known substance are separately excited.

FIG. 3 illustrates a simplified, alternative embodiment of the invention wherein the excitation and collection paths are not counter-propagating, but rather, a separate beam 302 is used to irradiate a point 304 along a collection path. Such a situation might correspond to point 142 in FIG. 1B. As shown by broken line 310, the excitation beam may be split off and used for simultaneous excitation of a point of the sample "S" at point 312. Other embodiments are also possible according to the invention, so long as a collection path contains spectra representative of a sample and a test region, with analytical instrumentation being used to detect the absolute or relative intensities associated therewith.

FIGS. 4A–4D plot wave number as a function of intensity with respect to a sample under investigation and a volume containing a known substance, in this case hydrogen, to show how changes in the various peaks may be indicative of a leak.

FIG. 4A illustrates a situation wherein spectra 402 are representative of a sample, and peak 404 is representative of nitrogen as a known test substance. FIG. 4B illustrates the case wherein a small amount of one constituent 406 has leaked into the test region 222, thereby causing a slightly lower response of the nitrogen peak 404. It may also happen that one of the peaks 402 associated with the sample material may increase slightly as the peak for nitrogen diminishes, enabling the ratio of sample to known substance to be used in a leak-detection procedure.

FIG. 4C illustrates the case wherein air has leaked into the chamber 222, resulting in a new peak 410. FIG. 4D illustrates a case wherein a series breach of nitrogen has occurred with respect to the containment volume, resulting in a total absence of the signature that was previously present for that material.

That claimed is:

1. A leak-detecting optical probe assembly for use with spectral analysis means, comprising:
   means for optically exciting at least a portion of a sample substance, the excitation causing wavelengths characteristic of the sample to be emitted along a collection path for reception by the spectral analysis means;
   a test region disposed in the collection path; and
   means for optically exciting a point within the test region, causing wavelengths characteristic of any substances within the test region to enter into the collection path.

2. The optical probe assembly of claim 1, including a single source of radiation used as the means for optically exciting the sample and the point within the test region.

3. The optical probe assembly of claim 2, wherein the single source of radiation is delivered along an excitation path which is counter-propagating with respect to the collection path.

4. The optical probe assembly of claim 1, wherein the test region is filled with a known substance.

5. The optical probe assembly of claim 4, wherein the known substance is a gas.

6. The optical probe assembly of claim 1, wherein the spectral analysis means uses the ratio of the emission of the substance within the test volume, if any, and that of the sample to determine leak integrity.

7. The optical probe assembly of claim 1, wherein the spectral analysis means is based upon Raman detection.

8. The optical probe assembly of claim 1, wherein the spectral analysis means is based upon fluorescence detection.

9. A leak-detecting remote optical probe assembly for use with spectral analysis means, the assembly comprising:
- a source of excitation radiation;
- a first optical fiber for delivering the excitation radiation to a sample, the excitation radiation causing wavelengths characteristic of the sample to be emitted along a collection path;
- a test substance disposed in the collection path, whereby excitation radiation present in the collection path causes wavelengths characteristic of the test substance to enter into the collection path; and
- a second optical fiber having a distal end to receive the wavelengths characteristic of the sample and the test substance, and a proximal end to deliver the wavelengths of both the sample and the test substance to the spectral analysis means.

10. The remote optical probe assembly of claim 9, including a single source of excitation radiation used to excite both the sample and the test substance.

11. The optical probe assembly of claim 10, wherein the single source of radiation is delivered along an excitation path which is counter-propagating with respect to the collection path.

12. The optical probe assembly of claim 9, wherein the test substance is a gas.

13. The optical probe assembly of claim 9, wherein the spectral analysis means detects the absolute value of the test substance to determine leak integrity.

14. The optical probe assembly of claim 9, wherein the spectral analysis means uses the ratio of the test substance and the sample to determine leak integrity.

15. The optical probe assembly of claim 9, wherein the spectral analysis means utilizes Raman detection.

16. The optical probe assembly of claim 9, wherein the spectral analysis means utilizes fluorescence detection.

* * * * *